United States Patent [19]
Kawasaki et al.

[11] Patent Number: 5,496,708
[45] Date of Patent: Mar. 5, 1996

[54] REAGENT COMPOSITION FOR QUANTITATIVE ANALYSIS OF INORGANIC PHOSPHOROUS AND DRY ANALYSIS ELEMENT UTILIZING THE SAME

[75] Inventors: Kazuya Kawasaki; Yoshikazu Amano; Osamu Seshimoto; Kiyoshi Yamada, all of Saitama, Japan

[73] Assignee: Fuji Photo Film Co., Ltd., Kanagawa, Japan

[21] Appl. No.: 259,616

[22] Filed: Jun. 14, 1994

[30] Foreign Application Priority Data

Jun. 15, 1993 [JP] Japan ..................... 5-167285

[51] Int. Cl.$^6$ .............. C12Q 1/28; G01N 31/22
[52] U.S. Cl. ............. 435/28; 435/805; 435/970; 422/56; 422/57
[58] Field of Search ............... 435/25, 28, 805, 435/969, 970; 422/56, 57; 436/170, 810; 544/268

[56] References Cited

U.S. PATENT DOCUMENTS 3,964,974  6/1976  Banauch ................. 195/103.5 C
3,992,158  11/1976  Przybylowicz ................ 23/253 TP
4,459,358  7/1984  Berke ........................ 436/170
4,861,552  8/1989  Masuda ....................... 422/56

OTHER PUBLICATIONS

The Merck Index 11th Ed. 1989 Merck & Co. Rahway NJ. pp. 9975–9976.

Sugiura M., An Enzymic Method for the . . . Japan J. Clin Chem vol. 11 #2 1982 pp. 83–87.

*Primary Examiner*—Ralph J. Gitomer
*Attorney, Agent, or Firm*—McAulay Fisher Nissen Goldberg & Kiel

[57] ABSTRACT

A reagent composition for the quantitative analysis of inorganic phosphorus, composted of xanthosine, purine nucleoside phosphorylase, xanthine oxidase and a color-former. The color-former is a precursor for forming a dye in the presence of hydrogen peroxide and peroxidase. The reagent composition of the invention is improved in storage stability and has a wider determination range. Also provided is a dry analysis element composed of reagent layer containing the inventive reagent composition.

10 Claims, 3 Drawing Sheets

5,496,708

REAGENT COMPOSITION FOR QUANTITATIVE ANALYSIS OF INORGANIC PHOSPHOROUS AND DRY ANALYSIS ELEMENT UTILIZING THE SAME

BACKGROUND OF THE INVENTION

1. Field of the Invention

The present invention relates to a reagent composition for the quantitative analysis of inorganic phosphorus or phosphate contained in a sample and a dry analysis element including a reagent layer containing such a reagent composition.

2. Prior Art Statement

The quantitative analysis of inorganic phosphorus contained in blood serum or urine is an effective clinical chemical test for finding the mineral or electrolyte metabolism, similar to the analysis of calcium in blood serum, and thus it is recognized as one of the important clinical tests for the examination of disorder in kidney function, vitamin D deficiency, acromegaly, hyperparathyroidism or hypoparathyroidism.

The quantitative analysis of inorganic phosphorus, which has been most frequently adopted in the art, is the phosphomolybdate reduction methods, the representative thereof being the Fiske-Subbarow method. In the phosphomolybdate reduction method, phosphate ions are allowed to react with a molybdate to produce phosphomolybdic acid, and then reduced by a reducing agent to be converted to molybdenum blue which is colorimetrically analyzed to effect quantitative analysis of inorganic phosphorus. However, this known method has disadvantages such that deproteinization operation, which is conducted by the addition of trichloroacetic acid or like reagent, is required. Further, the color stability after the development of color is relatively poor to require strict time control from the color development to the colorimetrical measurement. In addition, the reducing agent used in the coloring reaction has poor storage stability. These disadvantages induce inconvenience when the method is used for a clinical test wherein a lot of samples must be processed rapidly. This known method has further problems that metallic parts of the instruments used for analysis operation are corroded by the use of a strong acid and that formed dye pigments tend to be adsorbed to the vessels or lines of the instrument. These problems pose hard obstacles for the realization of automated analyzing system for the quantitative analysis of inorganic phosphorus.

Particularly in the routine clinical tests in which a number of test samples are to be handled, it is demanded that the individual samples should be analyzed rapidly by simple operations, more desirably by automated operation sequence. To comply with the demand, dry analysis elements have been proposed (for example, by Unexamined Japanese Patent Publication Nos. 53888/1974 (corresponding to U.S. Pat. No. 3,992,158), 77356/1984 (corresponding to EP 0097952A) and 102388/1984 (corresponding to U.S. Pat. No. 4,861,552) and U.S. Pat. No. 4,459,358. Although it is desirous that the phosphomolybdate reduction method can be applied to such a dry analysis element, it is difficult to realize such an application.

In recent years, a few enzymatic analysis methods, by which inorganic phosphorus can be specifically analyzed without the need of deproteinization or similar pre-treatment, has been developed (Japan J. Clin. Chem., 11, 83, (1982), Unexamined Japanese Patent Publication Nos. 210998/1985 and 74499/1988). One of such methods is the PNP-XOD-POD method disclosed, for example, by Japan J. Clin. Chem., 11, 83, (1982), wherein inorganic phosphate Pi is allowed to react with inosine in the presence of purine nucleoside phosphorylase (hereinafter referred to as PNP) to produce hypoxanthine which is oxidized by the action of xanthine oxidase (hereinafter referred to as XOD) to form xanthine which is further oxidized to uric acid, and wherein hydrogen peroxide ($H_2O_2$) produced at the oxidation step by the action of XOD is utilized for the color development of a color-former(dye precursor or chromogenic substrate) while using a peroxidase (hereinafter referred to as POD) and then the color density of the thus formed color is colorimetrically analyzed, the principle of this method being shown in FIG. 2. Since this method is a direct method wherein deproteinization is not required and is an enzymatic process in which no strong acid is used, there is no waste liquid problem otherwise arises in the conventional phosphomolybdate reduction method. This method is particularly convenient in that it is free from corrosion of automated analysis system and adsorption of formed dye pigment.

The PNP-XOD-POD method, as described above, may be applied to a dry analysis element. The dry analysis element is an analysis element including one or plural functional layers, at least one layer (or plural layers) of which contains an analytical reagent composition so as to form a coloring dye by the reaction taking place in the layer and the thus formed dye is colorimetrically analyzed by measuring the transmitting or reflecting light from the outside of the analysis element. Since such a dry analysis element is stored and preserved in the dry state prior to the analysis operation, there is no need of preparing the reagent at the measuring step. Furthermore, since the reagent has a higher stability in the dry state, the process using such a dry analysis element is improved in simplicity and speed of operation over the conventional wet process.

However, in the course of investigation for the realization of applying the aforementioned PNP-XOD-POD method to the dry analysis element, the inventors have found that there are problems in the storage stability and the measurable range.

OBJECTS AND SUMMARY OF THE INVENTION

After eager pursuits for solving the problems, the present invention has been accomplished based on the finding that the storage stability is remarkably improved and the measurable range is significantly broadened by the use of xanthosine in place of the conventionally used inosine as the substrate for PNP.

Accordingly a first object of the invention is to provide a reagent composition for the quantitative analysis of inorganic phosphorus, which is well suited for the preparation of a dry analysis element which is improved in storage stability and has a wide determination range. The first object of the invention is attained by the provision of a reagent composition for the quantitative analysis of inorganic phosphorus comprising xanthosine, purine nucleoside phosphorylase, xanthine oxidase, peroxidase and a color-former.

A second object of the invention is to provide a dry analysis element for the quantitative analysis of inorganic phosphorus, which is improved in storage stability and has a wide determination range. The second object of the invention is attained by the provision of a dry analysis element for the quantitative analysis of inorganic phosphorus comprising a reagent layer which contains xanthosine, purine nucleoside phosphorylase, xanthine oxidase, peroxidase and a color-former.

BRIEF DESCRIPTION OF APPENDED DRAWINGS

The presently preferred embodiments of the invention will now be described with reference to the appended drawings, in which.

DETAILED DESCRIPTION OF PREFERRED EMBODIMENTS

Figure 1:
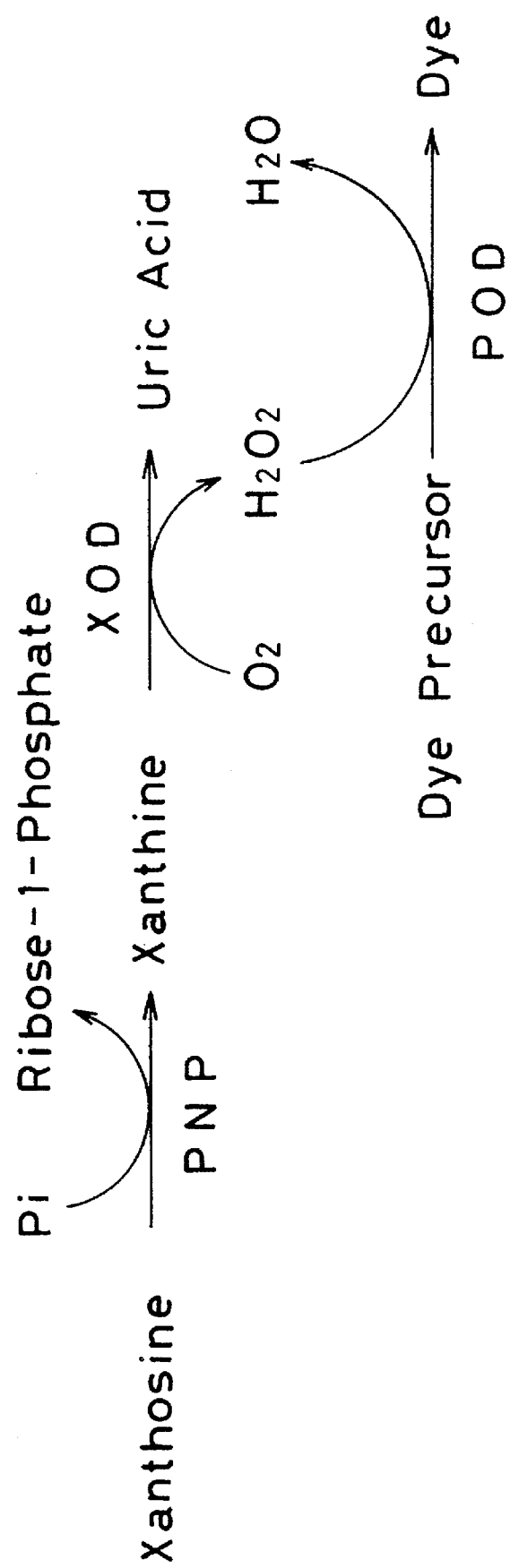
FIG. 1 is a diagram showing the reaction principle of the reagent composition used in the present invention for the quantitative analysis of inorganic phosphorus.
Figure 2:
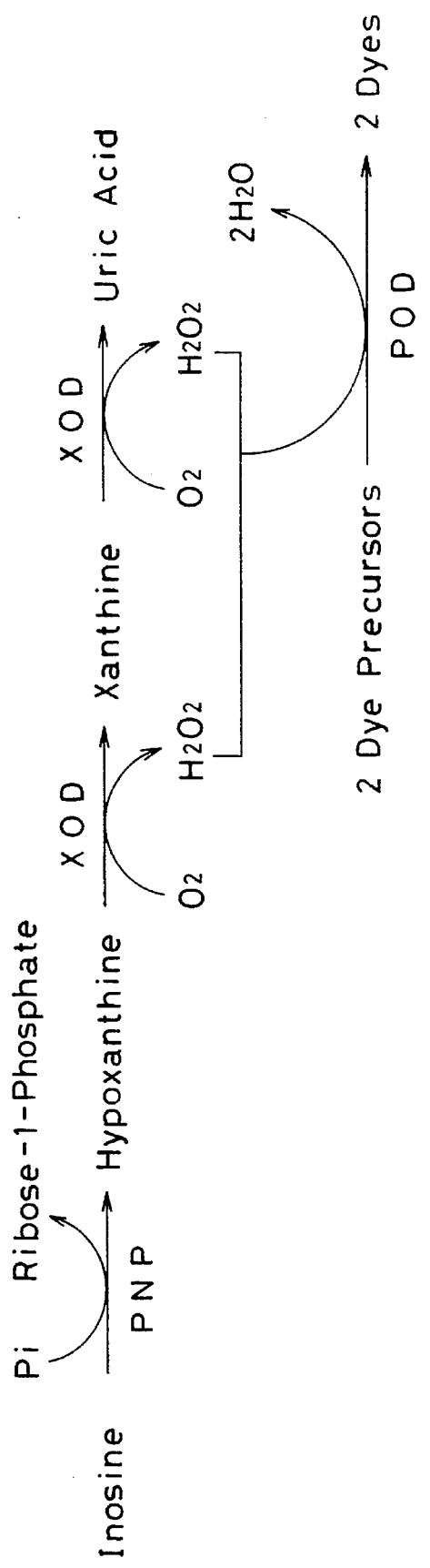
FIG. 2 is a diagram showing the reaction principle of the conventional reagent composition used in the prior art process wherein an enzymatic reaction is utilized.

The reaction principle of the reagent composition for the quantitative analysis, according to the invention, is shown in FIG. 1. As shown, inorganic phosphorus or phosphate (Pi) is allowed to react with xanthosine in the presence of purine nucleoside phosphorylase (PNP) to produce xanthine. Xanthine is oxidized by xanthine oxidase (XOD) to produce uric acid. At the later XOD reaction, hydrogen peroxide ($H_2O_2$) is also produced. Thus produced hydrogen peroxide reacts with and oxidizes a color-former (dye precursor or chromogenic substrate) by the action of peroxidase (POD) to produce a formed dye. The formed color is colorimetrically determined.

Meantimes, elementaly phosphorus does not exist to any appreciable extent in the body, and thus prior methods for the analysis of inorganic phosphorus have been directed toward the analysis of the two phosphate anions, which interchange rapidly depending on the pH. The monovalent and divalent anion forms are present in serum at about equal concentrations in acidosis, in a ratio of 1:9 in alkalosis, in a ratio of 1:4 at pH 7.4, and in a ratio of 100:1 in a pH 4.5 urine, making it impossible to say with any certainty what the molecular weight of inorganic "phosphate" is. Therefore, the units traditionally chosen have been milligrams or millimoles of phosphorus (in a volume) but never milliequivalents of phosphate, since that would change rapidly with the charge. Accordingly, the inorganic phosphorus, which can be analyzed by the reagent composition of the present invention, include monovalent phosphate anion ($H_2PO_4^-$), divalent phosphate anion ($HPO_4^{2-}$) and salts thereof.

The reagent composition and the dry analysis element containing the reagent composition, according to the present invention, is not limited only to the application for the quantitative analysis of inorganic phosphorus in the body fluids, such as serum, plasma and urine, but also may be applied for the quantitative analysis of inorganic phosphorus contained in various waste liquids (drainages of household use, drainages discharged from factories and drainages discharged from hospitals or research facilities). The reagent composition and the dry analysis element containing the reagent composition, according to the present invention, may be used for quantitatively analyzing inorganic phosphorus in a waste liquid to inspect the degree of contamination, for quantitatively analyzing inorganic phosphorus in natural water to determine whether it is suitable for drinking, or for quantitatively analyzing inorganic phosphorus contained in a water sample taken from a lake or river as an index for enrichment in nutrition. The reagent composition and the dry analysis element containing the reagent composition, according to the present invention, may also be used for quantitatively analyzing inorgnaic phosphorus contained in a drip from a fresh fish to know the freshness of the fish.

Commercially available purine nucleoside phosphorylase (PNP, EC 2.4.2.1), and commercially available xanthine oxidase (XOD, EC 1.2.3.2) and peroxidase (POD, EC 1.11.1.7) can be used in the invention. The color-former used in the invention may be one which forms a dye in the presence of hydrogen peroxide and peroxidase (POD), the examples being a composition forming a coloring matter or dye by the oxidation of a leuco dye, such as triaryl imidazole leuco dye disclosed in U.S. Pat. No. 4,089,747 and diaryl imidazole leuco dye disclosed in Unexamined Japanese Patent Publication No. 193352/1984 (EP 0 122 641A), and a composition containing a compound which forms a dye upon coupling with another compound when oxidized (such as a composition containing 4-aminoantipyrines and one of phenols or naphthols).

The reagent composition of the invention may contain another ingredient such as a buffer composition as desired. The suitable pH range of the reagent composition is preferably from 6.0 to 8.0, most preferably from 7.0 to 7.5. When the reagent composition is used for the preparation of a dry analysis element, it is desirable to use a surfactant.

The dry analysis element for the quantitative analysis of inorganic phosphorus, according to the invention, may have a layer structure similar to those of the known various dry analysis elements. An additional layer may be introduced to prepare a dry analysis element having the layer structure similar to that of a variety of the known dry analysis elements. In detail, in addition to the layer containing the reagent composition of the invention, the analysis element of the invention may have a multi-layered structure including a support member, a spreading layer, a detection layer, a light-shielding layer, an adhesive layer, a water-absorbing layer, an undercoating layer or other desired layers. The construction of multi-layer structure has been disclosed, for example in Unexamined Japanese Patent Publication No. 53888/1974 (corresponding to U.S. Pat. No. 3,992,158), Unexamined Japanese Patent Publication No. 40191/1976 (corresponding to U.S. Pat. No. 4,042,335), Unexamined Japanese Patent Publication No. 164356/1980 (corresponding to U.S. Pat. No. 4,292,272), Unexamined Japanese Patent Publication No. 4959/1986 (corresponding to EP-0166365A).

When a light-transmitting and water-impermeable support is used, the dry analysis element having the following construction may be used, although the present invention is not limited to the following constructions.

(1) a support, and a reagent layer superposed in this order;

(2) a support, a detection layer, and a reagent layer, superposed in this order;

(3) a support, a detection layer, a light-reflecting layer, and a reagent layer superposed in this order;

(4) a support, a second reagent layer, a light-reflecting layer, and a first reagent layer, superposed in this order;

(5) a support, a detection layer, a second reagent layer, a light-reflecting layer, and a first reagent layer superposed in this order.

In each of the structures (1) to (3) set forth

For above, the reagent layer may composed of plural layers. For example, the reagent layer may comprise a first reagent layer containing the substance xanthosine and PNP necessary for the PNP reaction shown in FIG. 1; a second reagent layer containing the enzyme XOD necessary for the XOD reaction shown in FIG. 1; and a third reagent layer containing POD and a color-former (dye precursor) necessary for the POD reaction shown in FIG. 1. Otherwise, the reagent layer may comprise two layers including a first reagent layer in which the PNP reaction takes place and a second reagent layer in which the XOD and POD reactions take place. In a further modified embodiment, the reagent layer comprises a first reagent layer in which the PNP and XOD reactions take place and a second reagent layer in which the POD reaction takes place.

A water-absorbing layer may be interposed between the support and the reagent layer (or the detection layer). Filtration layers may be interposed between adjacent layers. A spreading layer may be provided on the reagent layer, and an adhesive layer may be interposed between the spreading layer and the reagent layer.

Details of respective layers forming the multiple layer structures will now be described.

Support:

The support may be light-nontransmitting (opaque), light-semi-transmitting (translucent) or light-transmitting (transparent), and it is generally preferable that the support is light-trasmitting and water-impermeable. Preferable materials for the light-transmitting and water-impermeable support are polyethylene terephthalate and polystyrene. In general, an undercoating is provided or the support is subjected to hydrophilization treatment in order to firmly adhere the hydrophilic layer.

Reagent Layer:

The reagent layer contains the reagent composition for the quantitative analysis of inorganic phosphorus, provided by the present invention. In order to ensure water permeability of the reagent layer, it is preferred that the layer is a porous layer composed of a porous medium or a layer composed of a hydrophilic polymer binder. It is preferable that such a water permeable layer is a continuous layer made of a hydrophilic polymer binder. The specific hydrophilic polymer binder used to form the water permeable layer may be selected in view of the product (dye or pigment) produced in the reagent layer and the reagent composition contained in the reagent layer.

When a porous layer is used as the reagent layer, the porous layer may be fibrous or non-fibrous. As the fibrous material, filter paper, non-woven cloth, woven cloth (e.g. plain woven cloth), knitted cloth (e.g. tricot knitted cloth) or filter paper made of glass fibers may be used. Examples of the non-fibrous material may be either one of a membrane filter composed of cellulose acetate described in Unexamined Japanese Patent Publication No. 53888/1974 (corresponding to U.S. Pat. No. 3,992,158), or a particulate structure layer containing interconnected voids and composed of inorganic or organic fine particles as disclosed in Unexamined Japanese Patent Publication Nos. 53888/1974 (corresponding to U.S. Pat. No. 3,992,158), 90859/1980 (corresponding to U.S. Pat. No. 4,258,001) and 70163/1983 (corresponding to U.S. Pat. No. 4,486,537). A laminated structure made of partially bonded multiple porous layers may also be preferably used, examples of such structure being disclosed in Unexamined Japanese Patent Publication Nos. 4959/1986 (corresponding to U.S. Pat. No. 5,019,347 and EP 0166365A), 116258/1987, 138756/1987 (corresponding to EP 0226465A), 138757/1987 (corresponding to EP 0226465A) and 138758/1987 (corresponding to EP 0226465A).

The porous layer may be a spreading layer having a so-called metering function to spread a liquid over an area substantially in proportion to the volume of the liquid fed thereto. Preferable materials for the spreading layer are woven and knitted fabrics. The woven fabrics or like may be subjected to the glow discharge treatment as described in Unexamined Japanese Patent Publication No. 66359/1982 (corresponding to U.S. Pat. No. 4,783,315 and GB 2,087, 974A). In order to adjust the area or rate for spreading, the spreading layer may contain a hydrophilic polymer or a surfactant as described in Unexamined Japanese Patent publication Nos. 222770/1985 (corresponding to EP 0162301A), 219397/1988 (corresponding to U.S. Pat. No. 4,889,797, U.S. Pat. No. 4,916,059 and EP 0207406A), 112999/1988 (corresponding to U.S. Pat. No. 4,889,797, U.S. Pat. No. 4,916,059 and EP 0207406A) and 182652/ 1987 (corresponding to U.S. Pat. No. 4,889,797, U.S. Pat. No. 4,916,059 and EP 0207406A).

Meanwhile, it is a convenient process to prepare a dry analysis element of the invention by initially impregnating or coating the reagent composition of the invention into or on a porous membrane or like layer made of paper, cloth or high polymer material to prepare a reagent layer which is then allowed to adhere onto another water permeable layer, for example a detection layer, provided on a support through the step as disclosed by Unexamined Japanese Patent Publication No. 164356/1980 (corresponding to U.S. Pat. No. 4,292,272).

Although the thickness of the reagent layer made by any of the aforementioned methods is not limited, the thickness may range within 1 µm to 50 µm, and preferably, from 2 µm to 30 µm, when the layer is provided as a coating layer. When it is provided by another method, for example by piling of a laminate, the thickness thereof may be varied within a wide range of from several tens of µm to several hundreds of µm.

When the reagent layer is composed of a water permeable layer made of a hydrophilic polymer binder, the usable hydrophilic binder may be gelatin and derivatives thereof (e.g. phthalated gelatin), derivatives of cellulose (e.g. hydroxyethyl cellulose ), agarose, sodium alginate, acrylamide copolymers, methacrylamide copolymers, copolymers of acryl amides or methacrylamides with various vinyl monomers, polyhydroxyethyl me thacrylate, polyvinyl alcohol, polyvinyl pyrrolidone, sodium polyacrylate, and copolymers of acrylic acid with various vinyl monomers.

The reagent layer composed of a hydrophilic polymer binder may be provided by coating an aqueous solution or dispersion of the present reagent composition and a hydrophilic polymer binder on another layer, such as a support or a detection layer, and then drying the coated solution or dispersion, as disclosed in the specifications of Japanese Patent Publication No. 21677/1988 (corresponding to U.S. Pat. No. 3,992,158 ), Unexamined Japanese Patent Publication Nos. 164356/1980 (corresponding to U.S. Pat. No. 4,292,272), 101398/1979 (corresponding to U.S. Pat. No. 4,132,528), and 292063/1986 (Chemical Abstracts, 106, 210567y). The thickness of the dried substrate layer containing a hydrophilic polymer as the binder may range from about 2 µm to about 50 µm, and preferably, from about 4 µm to about 30 µm, and the coverage thereof may range from about 2 g/m$^2$ to about 50 g/m$^2$, and preferably, from about 4 g/m$^2$ to about 30 g/m$^2$.

To improve the characteristics, such as, coating characteristics, diffusibility of the diffusible material, reactivity and storage stability, the reagent layer may include, in addition to the present reagent composition, various organic or inorganic additives, for example, enzyme activators, coenzymes, surfactants, pH buffer reagents, fine particles, antioxidants, etc. Examples of buffer system, which may be contained in the reagent layer, include pH buffer reagents as described in "KAGAKU BINRAN, KISOHEN" edited by Japanese Chemical Society (MARUZEN, Tokyo, 1966), pp1312–1320; R. M. C. Dawson et al., "Data for Biochemical Research", 2nd Edition (Oxford at the Clarendon Press, 1969), pp476–508; "Biochemistry", 5, pp467–477 (1966); and "Analytical Biochemistry", 104, pp300–310 (1980 ). Specific examples of usable buffers are buffer reagents containing borates, buffer reagents containing citric acid or citrates, buffer reagents containing glycine, buffer solutions containing Bicine, buffer reagents containing HEPES (2-hydroxyethylpiperazine-N'-2-ethanesulfonic acid), and buffer reagents containing Good's buffer agent such as MES (2-morpholinoethanesulfonic acid). Buffer compositions containing phosphates cannot be used in the reagent composition for the quantitative analysis of inorganic phosphorus according to the present invention.

The dry analysis element of the invention may be prepared by any of the known processes described in the specifications of the aforequoted patents.

The analysis element of the invention may be cut into a square piece having sides each ranging from about 10 to about 30 mm or a disk having a substantially same area. It is preferred, in view of the preparation, packaging, shipping, storage and measuring operations, that the element be contained in a slide frame as described, for example, in Japanese Patent Publication No. 28331/1982 (corresponding to U.S. Pat. No. 4,169,751), Unexamined Japanese Utility Model Publication No. 142454/1981 (corresponding to U.S. Pat. No. 4,387,990), Unexamined Japanese Patent Publication No. 63452/1982, Unexamined Japanese Utility Model Publication No. 32350/1983 and Unexamined Japanese Patent Publication No. 501144/1983 (corresponding to International Publication WO 83/00391) for use as a slide for chemical analysis. For the convenience in some uses, it may be formed in a long tape shape which is contained in a cassette or magazine, or a small piece thereof may be applied on or contained in a card having an opening.

The analysis element of the invention may be used for the quantitative analysis of inorganic phosphorus contained in a sample liquid by using it through the operations described in the specifications of the aforequoted patents. For example, about 2 μl to about 30 μl, preferably 4 μl to 15 μl, of an aqueous sample liquid, such as, serum, plasma or urine, is spotted or otherwise fed on the reagent layer. The analysis element spotted with the sample liquid is then incubated at a constant temperature of from about 20° C. to about 45° C., preferably at a constant temperature of from about 30° C. to about 40° C., for 1 to 10 minutes. The reflection optical density of the color or the change in color in the element may be measured from the light-transmitting support side, and the quantity of the inorganic phosphorus contained in the sample can be determined using a preliminarily prepared calibration curve based on the principle of colorimetry. The volume of the spotted liquid sample and the time and temperature for incubation are maintained constant to improve the accuracy in quantitative analysis.

The measuring operation may be carried out while using the chemical analysis apparatus described in Unexamined Japanese Patent Publication Nos. 125543/1985, 220862/ 1985, 294367/1986 and 161867/1983 (corresponding to U.S. Pat. No. 4,424,191) to realize a quantitative analysis at a high accuracy by extremely easy operations. Meantime, a simi-quantitative analysis may be conducted by judging the degree of coloring by naked eye if such visual judgment is adequate for the object or required accuracy.

EXAMPLES

Specific examples will be described hereinbelow for clear understanding of the invention.

Example 1

On a smooth sheet of colorless and transparent polyethylene terephthalate (PET) provided with a gelatin undercoating and having a thickness of 180 μm, coated was an aqueous solution of the composition (a) set forth in the following Table 1, followed by drying, to form a reagent layer so that respective components had the coverage as set forth in Table 1.

TABLE 1

| Composition (a) of Aqueous Reagent Solution | |
|---|---|
| Gelatin | 18.8 g/m² |
| p-Nonylphenoxy Polyxydol (Containing 10 (average) of Glycidol Unit; $C_9H_{19}$—$C_6H_4$—O—$(CH_2CH(OH)$—$CH_2$—$O)_{10}H)$ | 1.5 g/m² |
| Xanthosine | 1.96 g/m² |
| Peroxidase | 15,000 IU/m² |
| Xanthine Oxidase | 13,600 IU/m² |
| Purine Nucleoside Phosphorylase | 3,400 IU/m² |
| Leuco Dye (2-(3,5-dimethoxy-4-hydroxyphenyl)-4-phenetyl-5-(4-dimethylaminophenyl) imidazole) | 0.28 g/m² |
| Water (Adjusted to have a pH value of 6.8 by the use of a dilute NaOH solution) | 136 g/m² |

An adhesive layer was formed by coating an aqueous solution having the composition (b) as set forth in the following Table 2, followed by drying, so that respective components had the coverages as set forth in Table 2.

TABLE 2

| Composition (b) of Aqueous Adhesive Solution | |
|---|---|
| Gelatin | 3.1 g/m² |
| p-Nonylphenoxy Polyxydol (Containing 10 (average) of Glycidol Unit; $C_9H_{19}$—$C_6H_4$—O—$(CH_2CH(OH)$—$CH_2$—$O)_{10}H)$ | 0.25 g/m² |
| Water | 59 g/m² |

Thereafter, a porous spreading layer was provided by supplying water over the entire surface of the adhesive layer at a spreading rate of 30 g/m² to swell the gelatin layer, followed by laminating a broad fabric of pure polyester by slightly pressing uniformly the fabric on the adhesive layer.

Finally, an aqueous solution of a composition (c) as set forth in the following Table 3 was coated over the spreading layer, so that respective components had the coverages as set forth in Table 3, followed by drying to prepare an integral multi-layered analysis element for the quantitative analysis of inorganic phosphorus according to the embodiment of the invention.

TABLE 3

| Composition (c) of Aqueous Solution for Coating over the Spreading Layer | |
|---|---|
| HEPES | 2.1 g/m² |
| Hydroxypropylmethyl Cellulose | 0.9 g/m² |

TABLE 3-continued

Composition (c) of Aqueous Solution for
Coating over the Spreading Layer

| | |
|---|---|
| (Containing 19% to 24% of methoxy group and 4% to 12% of hydroxypropoxy group, and the viscosity of a 2% aqueous solution thereof being 80 to 120 cps at 20° C.) | |
| Surface Active Agent | 2.7 g/m² |
| (Polyoxyethylene Octyl Phenyl Ether; $(C_8H_{17}\text{—}C_6H_4\text{—}(O\text{—}CH_2\text{—}CH_2\text{—})_{40}OH)$ | |
| Titanium Dioxide (Rutile Type) | 4.2 g/m² |
| Water | 90.0 g/m² |
| (Adjusted to have a pH value of 7.5 by the use of a dilute NaOH solution) | |

Comparative Example

As a comparative example for comparing with the example of the invention, a comparative or control analysis element for the quantitative analysis of inorganic phosphorus was prepared similar to the preceding embodiment except that a composition (a') as set forth in the following Table 4 was used in place of the aqueous solution having the composition (a) for forming the reagent layer of the invention.

TABLE 4

Composition (a') of Aqueous Solution for
Forming Reagent Layer of Comparative Example

| | |
|---|---|
| Gelatin | 18.8 g/m² |
| p-Nonylphenoxy Polyxydol | 1.5 g/m² |
| (Containing 10 (average) of Glycidol Unit; $C_9H_{19}\text{—}C_6H_4\text{—}O\text{—}(CH_2CH(OH)\text{—}CH_2\text{—}O)_{10}H)$ | |
| Inosine | 1.85 g/m² |
| Peroxidase | 15,000 IU/m² |
| Xanthine Oxidase | 13,600 IU/m² |
| Purine Nucleoside Phosphorylase | 3,400 IU/m² |
| Leuco Dye | 0.28 g/m² |
| (2-(3,5-dimethoxy-4-hydroxyphenyl)-4-phenetyl-5-(4-dimethylaminophenyl) imidazole) | |
| Water | 136 g/m² |
| (Adjusted to have a pH value of 6.8 by the use of a dilute NaOH solution) | |

Measurement Example 1

Respective analysis elements were subjected to accelerated storage stability test to know the storage stabilities of the analysis element prepared in accordance with the Example of the invention and the Comparative Example. In detail, each of the analysis elements was stored for 0, 1, 4 and 7 days immediately after the preparation thereof in an incubator maintained at a temperature of 45° C.

From a human blood serum, the titer of which had been determined by using the "Phosphor B-Test Wako" (produced by Wako Pure Chemicals Co., Ltd.) which was a commercially available kit for the determination of inorganic phosphorus according to the phosphomolybdate reduction method, serum test samples each having a concentration of 2.5, 5.0, 10.0 and 20.0 mg/dl were prepared. Meanwhile, the concentration of inorganic phosphorus is the concentration of phosphorus converted into the concentration of P (elementary phosphorus). 10 μl for each of the test samples was spotted on each of the analysis elements. Each of the analysis elements thus spotted with serum samples was incubated at 37° C. for 6 minutes, and then the optical density of the reflected light having a wavelength of 650 nm was measured from the support side. The test results were compared to a calibration curve, which had been drawn by plotting the reflected optical densities obtained by measuring the incubated control serum samples, to know the apparent concentrations of inorganic phosphorus determined by the use of the analysis elements of the invention and the comparative example. The results are shown in the following Table 5.

TABLE 5

| Concentration of Inorganic Phosphorus (mg/dl) | Storage Period (days) | Example of the Invention (mg/dl) | Comparative Example (mg/dl) |
|---|---|---|---|
| 2.5 | 0 | 2.5 | 2.5 |
| | 1 | 2.5 | 2.5 |
| | 4 | 2.5 | 2.5 |
| | 7 | 2.5 | 2.5 |
| 5.0 | 0 | 5.0 | 5.0 |
| | 1 | 4.9 | 5.1 |
| | 4 | 5.0 | 5.1 |
| | 7 | 4.9 | 5.3 |
| 10.0 | 0 | 10.0 | 10.0 |
| | 1 | 9.7 | 11.8 |
| | 4 | 9.8 | 13.1 |
| | 7 | 9.8 | 14.0 |
| 20.0 | 0 | 20.0 | 18.6 |
| | 1 | 19.3 | 24.4 |
| | 4 | 19.7 | 31.3 |
| | 7 | 20.2 | 32.2 |

As will be seen from Table 5, The analysis element of the Comparative Example gave results which were scattered with large errors, the errors being increased as the concentrations of the samples became higher. In contrast thereto, the errors of the results found by the use of the analysis element of the invention were extremely smaller even when the analysis element was used after it was stored at 45° C. for 7 days. The result revealed that the analysis element of the invention is improved in storage stability as compared to the analysis element of the Comparative Example.

Measurement Example 2

The following tests were conducted to know the determination ranges of the analysis elements prepared in accordance with the Example of the invention and the Comparative Example.

From a human blood serum, the titer of which had been determined by using the "Phosphor B-Test Wako" (produced by Wako Pure Chemicals Co., Ltd.) which was a commercially available kit for the determination of inorganic phosphorus according to the phosphomolybdic acid reduction method, serum test samples each having a concentration of 2.5, 5.0, 10.0 and 20.0 mg/dl (converted into the concentration of elementary phosphorus) were prepared. 10 μl for each of the test samples was spotted on each of the analysis elements. Each of the analysis elements thus spotted with serum samples was incubated at 37° C. for 6 minutes, and then the optical density of the reflected light ($OD_R$) having a wavelength of 650 nm was measured from the backside of the support. The results are shown in the following Table 6.

TABLE 6

| Concentration of Inorganic Phosphorus (mg/dl) | $OD_R$ (Example of the Invention) | $OD_R$ (Comparative Example) |
| --- | --- | --- |
| 0 | 0.286 | 0.334 |
| 2.5 | 0.574 | 0.776 |
| 5.0 | 0.761 | 1.015 |
| 10.0 | 1.015 | 1.254 |
| 20.0 | 1.348 | 1.410 |

Figure 3:
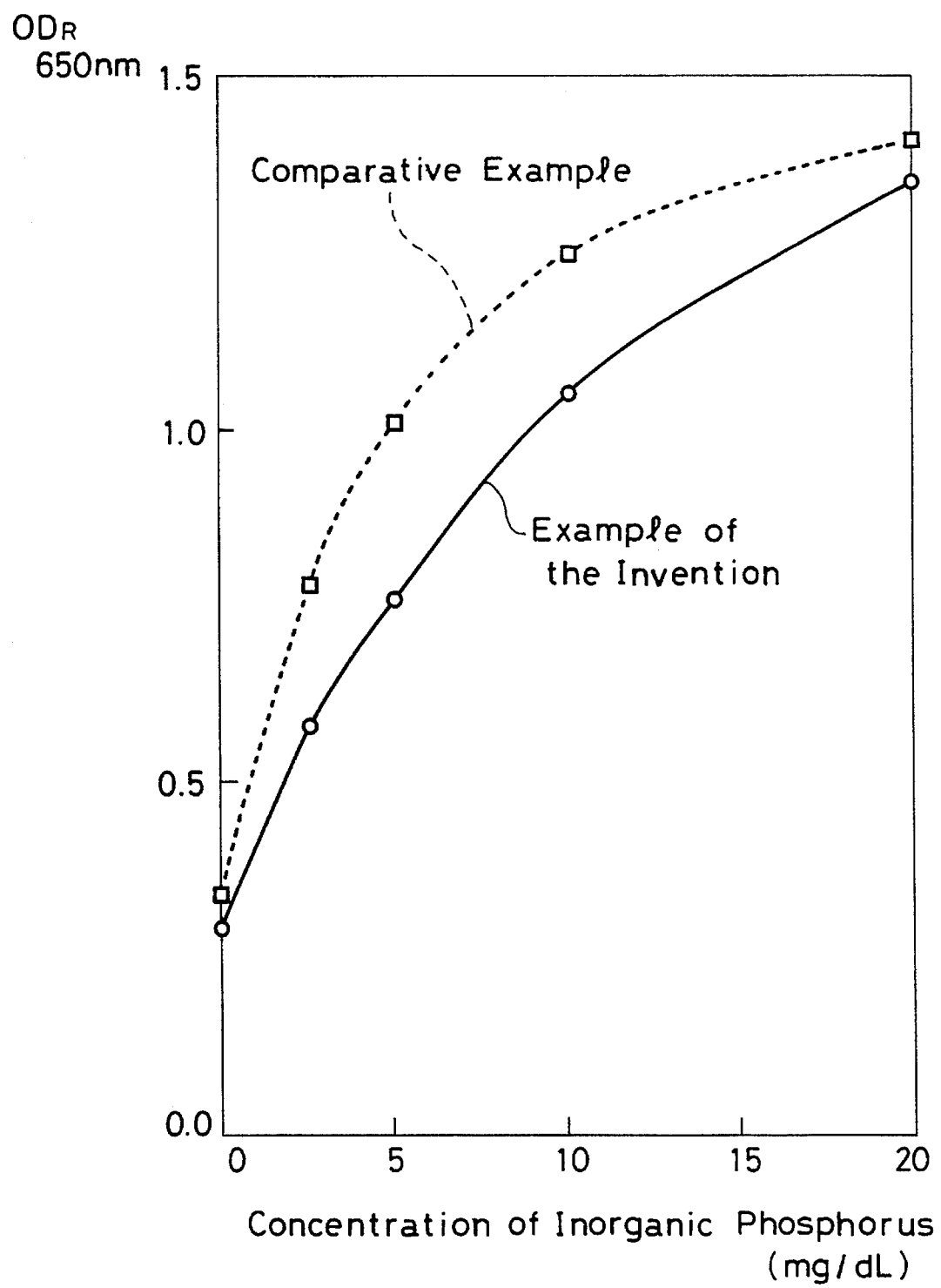
FIG. 3 is a graphic representation showing calibration curves, respectively, obtained as the results of determinations in an example of the invention and a comparative example according to the conventional technology.

The results as set forth in Table 6 were plotted to obtain a calibration curve shown by the graph in FIG. 3. As will be apparent from FIG. 3, in the Comparative Example, since the optical density of the reflected light per a unit concentration of inorganic phosphorus becomes smaller in the range of above 10 mg/dl, the accuracy in quantitative analysis of inorganic phosphorus in the high concentration range is deteriorated.

On the contrary, in the example of the invention, the optical density of the reflected light per a unit concentration of inorganic phosphorus is maintained at a high level throughout the range of above 10 mg/dl to give an accurate result within a higher concentration range. It is thus appreciated that the dry analysis element for the quantitative analysis of inorganic phosphorus, according to the invention, can be adopted for the quantitative analysis of inorganic phosphorus in a wider determination range as compared to the case in which the conventional reagent composition for a wet process quantitative analysis is adopted to prepare a dry analysis element.

As has been described hereinbefore, xanthosine is used for the substrate for purine nucleoside phosphorylase in the reagent composition provided by the invention. As an advantageous result, when the reagent composition of the invention is used for the preparation of a dry analysis element, the storage stability is improved and the determination range is broadened remarkably.

What is claimed is:

1. A reagent composition for the quantitative analysis of inorganic phosphorus comprising xanthosine, purine nucleoside phosphorylase, xanthine oxidase, peroxidase and a color-former, said color-former being a precursor for forming a dye in the presence of hydrogen peroxide produced by said xanthine oxidase and said peroxidase.

2. The reagent composition of claim 1, further comprising a buffer composition for maintaining the aqueous solution of said reagent composition within a pH range of from 6.0 to 8.0.

3. The reagent composition of claim 1, wherein said color-former is selected from the group consisting of a leuco dye, and a composition containing a compound which forms a dye upon coupling with another compound when oxidized.

4. A dry analysis element for the quantitative analysis of inorganic phosphorus comprising a reagent layer which contains xanthosine, purine nucleoside phosphorylase, xanthine oxidase, peroxidase and a color-former, said color-former being a precursor for forming a dye in the presence of hydrogen peroxide produced by said xanthine oxidase and said peroxidase.

5. The dry analysis element of claim 4, wherein said element has a multi-layer structure comprising, in addition to said reagent layer, any one or more of a support, a spreading layer, a detection layer, a light-shielding layer, an adhesive layer, a water absorbing layer and an undercoating layer.

6. The dry analysis element of claim 4, wherein said reagent layer is partitioned into plural layers including a first reagent layer containing said xanthosine and said purine nucleoside phosphorylase, a second reagent layer containing said xanthine oxidase and a third reagent layer containing said peroxidase and said color-former.

7. The dry analysis element of claim 4, wherein said reagent layer is partitioned into two layers including a first reagent layer containing said xanthosine and said purine nucleoside phosphorylase and a second reagent layer containing said xanthine oxidase, said peroxidase and said color-former.

8. The dry analysis element of claim 4, wherein said reagent layer is partitioned into two layers including a first reagent layer containing said xanthosine, said purine nucleoside phosphorylase and xanthine oxidase, and a second reagent layer containing said peroxidase and said color-former.

9. The dry analysis element of claim 4, wherein said reagent layer comprises a water-permeable layer, a material for said water-permeable layer being selected from the group consisting of porous materials and hydrophilic polymer binders.

10. The dry analysis element of claim 4, wherein said color-former is selected from the group consisting of a leuco dye, and a composition containing a compound which forms a dye upon coupling with another compound when oxidized.

* * * * *